(12) United States Patent
Dubois et al.

(10) Patent No.: US 8,258,168 B2
(45) Date of Patent: Sep. 4, 2012

(54) 2H OR 3H-BENZO[E]INDAZOL-1-YL CARBAMATE DERIVATIVES, THE PREPARATION AND THERAPEUTIC USE THEREOF

(75) Inventors: Laurent Dubois, Le Piessis-Robinson (FR); Yannick Evanno, Bullion (FR); Christian Maloizel, Meudon (FR); Mireille Sevrin, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/348,241

(22) Filed: Jan. 11, 2012

(65) Prior Publication Data
US 2012/0108584 A1    May 3, 2012

Related U.S. Application Data

(63) Continuation of application No. 12/360,535, filed on Jan. 27, 2009, now Pat. No. 8,114,899, which is a continuation of application No. 11/549,293, filed on Oct. 13, 2006, now Pat. No. 7,501,449, which is a continuation of application No. PCT/FR2005/001154, filed on May 10, 2005.

(30) Foreign Application Priority Data

May 11, 2004 (FR) ..................................... 04 05055

(51) Int. Cl.
*A61K 31/416* (2006.01)
*C07D 231/54* (2006.01)

(52) U.S. Cl. .................. 514/403; 548/356.1; 548/358.1; 548/359.1

(58) Field of Classification Search ............... 548/356.1, 548/358.1, 359.1; 514/403
See application file for complete search history.

(56) References Cited

U.S. PATENT DOCUMENTS 7,501,449 B2    3/2009   DuBois et al.
8,114,899 B2 *  2/2012   DuBois et al. ................ 514/406

FOREIGN PATENT DOCUMENTS

| EP | 0607076 | 7/1994 |
|----|---------|--------|
| EP | 1036794 | 9/2000 |
| FR | 2741073 | 12/1997 |
| WO | WO 99/58117 | 11/1999 |

OTHER PUBLICATIONS

Lloyd, G.K., et. al., The Activity of Zolpidem and Other Hypnotics Within the γ-Aminobutyric Acid (GABAA) Receptor Supramolecular Complex, as Determined by 35 S-t-Butylbicyclophosphorothionate (35S-TBPS) Binding to Rat Cerebral Cortex Membranes, Journal of Pharmacology and Experimental Therapeutics. vol. 255, No. 2 (1990) pp. 690-696.

Nakao, T., et. al., Synthesis and Biological Activities of Optical Isomers of 2-(4-Chlorophenyl)-5,6-dihydro-(1) benzo-thiepino[5,4-c]Pyridazin-3(2H)-one 7-Oxide. Chem. Pharm. Bull. vol. 40, No. 1 pp. 117-121 (1992).

Olivier, A., et. al., A Conformational Study of Ligands for Omega Modulatory Sites of GabaA Receptors by Noesy NMR Spectroscopy and Distance Geometry, Bioorganic & Medicinal Chemistry Letters, vol. 7, No. 17. pp. 2277-2282 (1997).

Piperaki, S., et. al., Enantiomeric Separation of Zopiclone, its Metabolites and Products of Degradation on a B-Cyclodextrin Bonded Phase, Journal of Chromatography A, vol. 729, (1996) pp. 19-28.

Rao, V., et. al., Characterization of Binding Sites for the w3 Receptor Ligands [3H]PK11195 and [3H]RO5-4864 in Human Brain, European Journal of Pharmacology vol. 340, (1997) pp. 89-99.

Weissman, B.A., et. al., Presence of Peripheral Benzodiazepine Binding Sites on Primary Rat Skeletal Fibroblasts, European Journal of Pharmacology vol. 187, Issue 3, (1990) pp. 369-375 abstract.

Yokoyama, N., et al., 2-Arylpyrazolo[4,3-c]quinolin-3-Ones: Novel Agonist, Partial Agonist, and Antagonist of Benzodiazepines, J. Med. Chem. (1982) vol. 25, pp. 337-339.

International Search Report for WO2005/121099 dated Dec. 22, 2005.

U.S. Appl. No. 12/360,535, filed Jan. 27, 2009.
U.S. Appl. No. 11/549,293, filed Oct. 13, 2006.

* cited by examiner

*Primary Examiner* — Golam M M Shameem
(74) *Attorney, Agent, or Firm* — Kelly L. Bender

(57) ABSTRACT

Compounds corresponding to the formula (I)

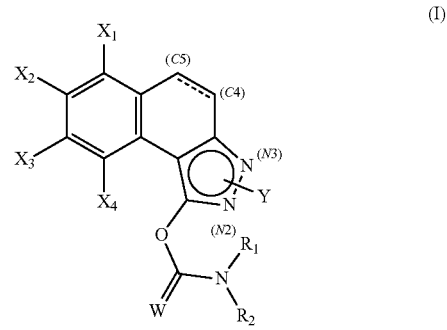

as defined in the disclosure, as well as methods for making such compounds, intermediates employed in such methods, pharmaceutical compositions containing the compounds of the invention, and methods of treatment using them.

2 Claims, No Drawings

2H OR 3H-BENZO[E]INDAZOL-1-YL CARBAMATE DERIVATIVES, THE PREPARATION AND THERAPEUTIC USE THEREOF

CROSS-REFERENCE TO RELATED APPLICATIONS

This application is a continuation of U.S. application Ser. No. 12/360,535, filed Jan. 27, 2009, now allowed, which is a continuation of U.S. application Ser. No. 11/549,293, filed Oct. 13, 2006, now U.S. Pat. No. 7,501,449, which is a continuation of PCT/FR2005/001154, filed May 10, 2005, which claims priority from FR Patent Application No. 04/05055, filed May 11, 2004.

SUMMARY OF THE INVENTION

A subject-matter of the invention is 2H— or 3H-benzo[e]indazol-1-yl carbamate derivative compounds which exhibit an in vitro and in vivo affinity for peripheral-type benzodiazepine receptors (PBR or p sites).

A first subject-matter of the invention is the compounds corresponding to the general formula (I) below.

Another subject-matter of the invention is processes for the preparation of the compounds of general formula (I).

Another subject-matter of the invention is the uses of the compounds of general formula (I), in particular in medicaments or in pharmaceutical compositions.

DETAILED DESCRIPTION OF THE INVENTION

The compounds of the invention correspond to the general formula (I):

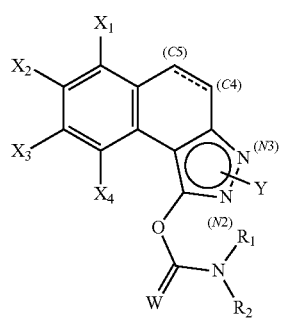

in which
W represents an oxygen or sulphur atom;
$X_1$, $X_2$, $X_3$ and $X_4$ each represent, independently of one another, a hydrogen or halogen atom or a cyano, $C_1$-$C_6$-alkyl, $C_1$-$C_6$-fluoroalkyl, $C_1$-$C_6$-alkoxy or $C_1$-$C_6$-fluoroalkoxy group;
Y is in the (N2) or (N3) position;
when Y is in the (N2) position, Y represents a $C_1$-$C_6$-alkyl, $C_1$-$C_6$-fluoroalkyl, aryl or heteroaryl group;
when Y is in the (N3) position, Y represents an aryl or heteroaryl group;
the aryl or heteroaryl groups optionally being substituted by one or more atoms or groups chosen from halogen atoms or $C_1$-$C_6$-alkyl, $C_1$-$C_6$alkoxy, $C_1$-$C_6$-alkylthio, $C_1$-$C_6$-alkyl-S(O)—, $C_1$-$C_6$-alkyl-S(O)$_2$— or $C_1$-$C_6$-fluoroalkyl groups;
the bond in the $C_4$-$C_5$ position is a double or single bond;

$R_1$ and $R_2$ each represent, independently of one another, an aryl, benzyl or $C_1$-$C_6$-alkyl group; or else $R_1$ and $R_2$ form, with the nitrogen atom which carries them, a heterocycle optionally substituted by one or more $C_1$-$C_6$-alkyl or benzyl groups.

In the context of the present invention:
$C_t$-$C_z$ where t and z can take the values from 1 to 6, is understood to mean a carbon chain which can have from t to z carbon atoms, for example $C_{1-3}$, a carbon chain which can have from 1 to 3 carbon atoms;
an alkyl is understood to mean a saturated, linear or branched, aliphatic group. Mention may be made, by way of examples, of the methyl, ethyl, propyl, isopropyl, butyl, isobutyl, tert-butyl or pentyl groups, and the like;
a fluoroalkyl is understood to mean an alkyl group, one or more hydrogen atoms of which have been substituted by a fluorine atom;
an alkoxy is understood to mean an —O-alkyl radical where the alkyl group is as defined above;
a fluoroalkoxy is understood to mean an alkoxy group, one or more hydrogen atoms of which have been substituted by a fluorine atom;
an alkylthio is understood to mean an —S-alkyl radical where the alkyl group is as defined above;
a heterocycle is understood to mean a 4- to 7-membered cyclic group comprising a nitrogen atom and optionally another heteroatom, such as nitrogen, oxygen or sulphur. Mention may be made, as examples of heterocycles, of the azetidinyl, pyrrolidinyl, piperidinyl, morpholinyl, thiomorpholinyl, azepinyl, piperazinyl or homopiperazinyl groups;
an aryl is understood to mean an aromatic cyclic group comprising between 6 and 10 carbon atoms. Mention may be made, as examples of aryl groups, of the phenyl or naphthyl groups;
a heteroaryl is understood to mean a 5- or 6-membered aromatic cyclic group comprising 1 or 2 heteroatoms, such as nitrogen, oxygen or sulphur. Mention may be made, as examples of heteroaryl groups, of the pyridyl, thienyl, furyl, pyrimidinyl, pyrazinyl or pyridazinyl groups;
a member is understood to mean, in a cyclic group, an atom connected to the two adjacent atoms of the ring;
a halogen atom is understood to mean a fluorine, a chlorine, a bromine or an iodine.

The compounds of general formula (I) can comprise one or more asymmetric carbons. They can exist in the form of enantiomers or of diastereoisomers. These enantiomers and diastereoisomers, and their mixtures, including the racemic mixtures, form part of the invention.

The compounds of formula (I) can exist in the form of bases or of addition salts with acids. Such addition salts form part of the invention.

These salts are advantageously prepared with pharmaceutically acceptable acids but the salts of other acids, for example of use in the purification or the isolation of the compounds of formula (I), also form part of the invention.

The compounds of general formula (I) can exist in the form of hydrates or of solvates, namely in the form of combinations or associations with one or more molecules of water or with a solvent. Such hydrates and solvates also form part of the invention.

Among the compounds of formula (I) which are subject-matters of the invention, a first subgroup of compounds is composed of the compounds for which:
W represents an oxygen or sulphur atom; and/or
$X_1$, $X_2$ and $X_3$ each represent, independently of one another, a hydrogen atom, a halogen atom, more particularly a fluorine, chlorine or bromine atom, a cyano group, a $C_1$-$C_6$-alkyl group, more particularly a methyl group, or a $C_1$-$C_6$-alkoxy group, more particularly a methoxy group; and/or $X_4$ represents a hydrogen atom; and/or Y is in the (N2) or (N3) position;

when Y is in the (N2) position, Y represents a $C_1$-$C_6$-alkyl group, more particularly a methyl or ethyl group, a $C_1$-$C_6$-fluoroalkyl group, more particularly a trifluoroethyl group, an aryl group, more particularly a phenyl group, or a heteroaryl group, more particularly a pyridyl or pyrazinyl group;

when Y is in the (N3) position, Y represents an aryl group, more particularly a phenyl group, or a heteroaryl group, more particularly a pyridyl or pyrimidinyl group;

the aryl or heteroaryl groups optionally being substituted by one or more atoms or groups, more particularly by one or two atoms or groups, chosen from halogen atoms, more particularly fluorine or chlorine atoms, $C_1$-$C_6$-alkyl groups, more particularly methyl groups, and $C_1$-$C_6$-alkoxy groups, more particularly methoxy groups; and/or the bond in the C4-C5 position is a double or single bond; and/or $R_1$ and $R_2$ each represent, independently of one another, an aryl group, more particularly a phenyl group, or a $C_1$-$C_6$-alkyl group, more particularly a methyl, ethyl, n-propyl, t-butyl or isopropyl group; or else $R_1$ and $R_2$ form, with the nitrogen atom which carries them, a heterocycle, more particularly pyrrolidinyl, piperidinyl, morpholinyl or piperazinyl, optionally substituted by one or two $C_1$-$C_6$-alkyl groups, more particularly methyl groups.

Among the compounds of formula (I) which are subject-matters of the invention, a second subgroup of compounds is composed of the compounds for which:

W represents an oxygen or sulphur atom; and/or $X_1$, $X_2$ and $X_3$ each represent, independently of one another, a hydrogen atom, a halogen atom, more particularly a fluorine, chlorine or bromine atom, a $C_1$-$C_6$-alkyl group, more particularly a methyl group, or a $C_1$-$C_6$-alkoxy group, more particularly a methoxy group; and/or $X_4$ represents a hydrogen atom; and/or Y is in the (N2) or (N3) position and represents an aryl group, more particularly a phenyl group, or a heteroaryl group, more particularly a pyridyl, pyrazinyl or pyrimidinyl group;

the aryl or heteroaryl groups optionally being substituted by one or more atoms or groups, more particularly by one or two atoms or groups, chosen from halogen atoms, more particularly fluorine or chlorine atoms, $C_1$-$C_6$-alkyl groups, more particularly methyl groups, and $C_1$-$C_6$-alkoxy groups, more particularly methoxy groups; and/or the bond in the C4-C5 position is a double or single bond; and/or $R_1$ and $R_2$ each represent, independently of one another, an aryl group, more particularly a phenyl group, or a $C_1$-$C_6$-alkyl group, more particularly a methyl, ethyl, n-propyl, t-butyl or isopropyl group; or else $R_1$ and $R_2$ form, with the nitrogen atom which carries them, a heterocycle, more particularly pyrrolidinyl, piperidinyl, morpholinyl or piperazinyl, optionally substituted by one or two $C_1$-$C_6$-alkyl groups, more particularly methyl groups.

Among the compounds of formula (I) which are subject-matters of the invention, a third subgroup of compounds is composed of the compounds for which:

W represents an oxygen or sulphur atom; and/or $X_1$, $X_2$ and $X_3$ each represent, independently of one another, a hydrogen atom, a halogen atom, more particularly a fluorine, chlorine or bromine atom, a $C_1$-$C_6$-alkyl group, more particularly a methyl group, or a $C_1$-$C_6$-alkoxy group, more particularly a methoxy group; and/or $X_4$ represents a hydrogen atom; and/or Y is in the (N3) position and represents an aryl group, more particularly a phenyl group, or a heteroaryl group, more particularly a pyridyl or pyrimidinyl group;

the aryl or heteroaryl groups optionally being substituted by one or more atoms or groups, more particularly by one or two atoms or groups, chosen from halogen atoms, more particularly fluorine or chlorine atoms, $C_1$-$C_6$-alkyl groups, more particularly methyl groups, and $C_1$-$C_6$-alkoxy groups, more particularly methoxy groups; and/or the bond in the C4-C5 position is a double or single bond; and/or $R_1$ and $R_2$ each represent, independently of one another, an aryl group, more particularly a phenyl group, or a $C_1$-$C_6$-alkyl group, more particularly a methyl, ethyl, t-butyl or isopropyl group; or else $R_1$ and $R_2$ form, with the nitrogen atom which carries them, a heterocycle, more particularly piperidinyl, optionally substituted by one or two $C_1$-$C_6$-alkyl groups, more particularly methyl groups.

The compounds of general formula (I) can be prepared by the processes illustrated in the following schemes.

According to a first preparation route (Scheme 1), a compound of general formula (II), in which $X_1$, $X_2$, $X_3$ and $X_4$ are as defined in the general formula (I), is reacted with methyl carbonate in the presence of a catalytic amount of a base, such as sodium methoxide or sodium hydride, to obtain the ketoester of general formula (III). The condensation of the ketoester (III) with hydrazine, for example in a polar solvent, such as DMF or acetic acid, makes it possible to isolate the pyrazole of general formula (IV). The latter is subsequently N-substituted nonselectively by the action of an aryl or heteroaryl halide of general formula Y-hal, in which Y is as defined in the general formula (I) and hal is a halogen atom, such as an iodine or a bromine, in the presence of a base, such as potassium or caesium carbonate, or of potassium triphosphate, of a catalytic amount of a copper salt and of a diamine (S. L. Buchwald, *J. Am. Chem. Soc.*, 2001, 123, 7727).

The resulting mixture composed of the positional isomers of general formulae (Va) and (Vb), in which the Y group is respectively in the 2-position and in the 3-position of the pyrazole ring, is subsequently derivatized by the action of a carbamoyl chloride derivative of general formula ClC(W)NR$_1$R$_2$, in which W, $R_1$ and $R_2$ are as defined in the general formula (I), in the presence of a base, such as potassium carbonate, sodium hydride or triethylamine, to obtain the carbamates of general formulae (Ia) and (Ib), which are separated, at this stage, by methods known to a person skilled in the art, such as chromatography on a silica column.

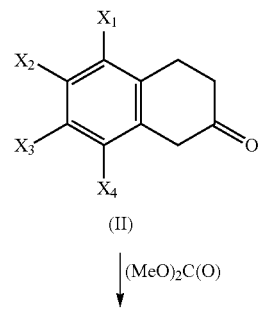

Scheme 1

(II)

↓ (MeO)$_2$C(O)

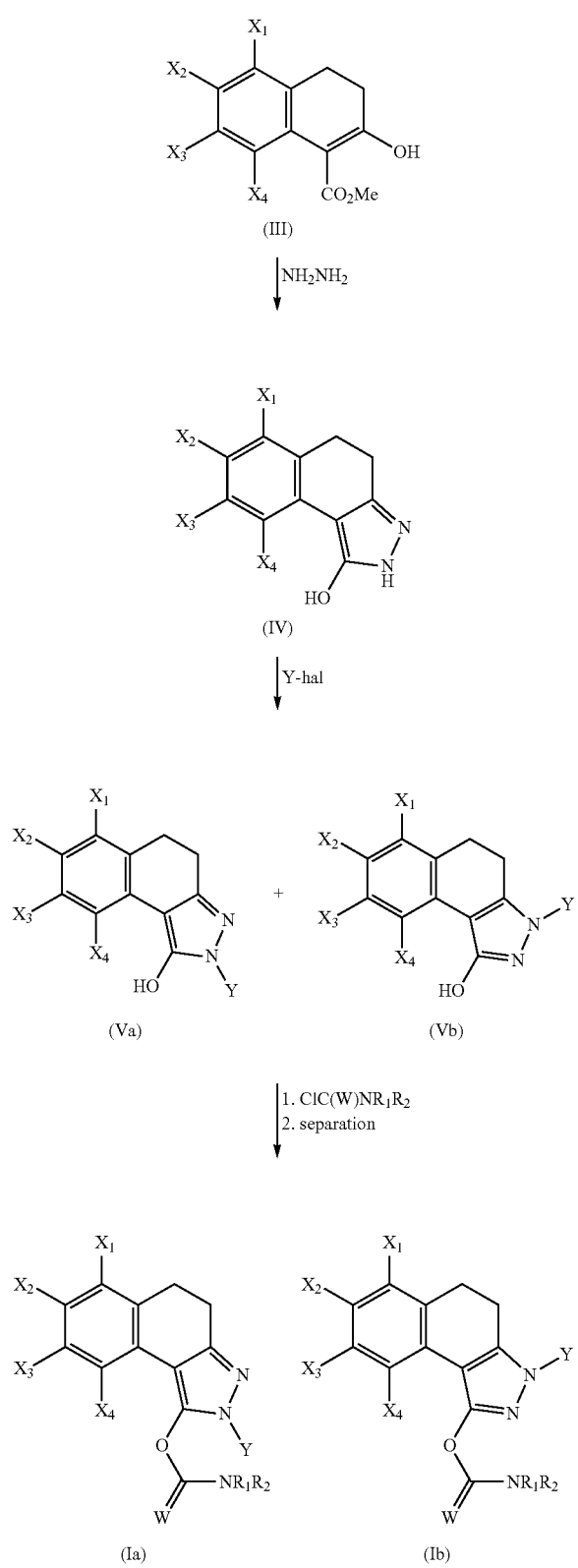

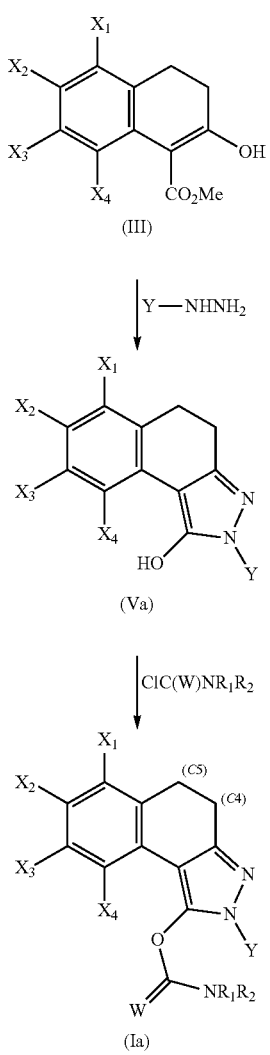

Alternatively, a second preparation route makes it possible to prepare the compounds of general formula (Ia) (Scheme 2).

It consists in condensing the ketoester of general formula (III), as defined above, with a hydrazine of general formula Y—NH—NH$_2$, in which Y is as defined in the general formula (I), for example in a polar solvent, such as DMF or acetic acid, and makes it possible to isolate the pyrazole of general formula (Va), as defined above. The latter is subsequently acylated by the action of a carbamoyl chloride derivative of general formula ClC(W)NR$_1$R$_2$, as defined above, in the presence of a base, such as potassium carbonate, sodium hydride or triethylamine, to obtain the carbamate of general formula (Ia).

The single bond in the C4-C5 position of the compounds of general formula (I) can optionally be dehydrogenated to form a double bond according to a method known to a person skilled in the art, for example by analogy with the method described by Kozo, Shishido et al., *Tetrahedron*, 1989, 45, 18, 5791-5804.

Alternatively, the compounds of general formula (I) comprising a single bond in the C4-C5 position can be dehydrogenated by reaction with a halogenating agent, such as N-bromosuccinimide, in the presence of an initiator, such as 2,2'-azobis(2-methylpropionitrile). Under these conditions, the compound of general formula (I) comprising a single bond in the C4-C5 position is first halogenated and then the resulting intermediate is subjected to an elimination reaction to result in the compound (I) comprising a double bond in the C4-C5 position.

In Schemes 1 and 2, the reactants, when their method of preparation is not described, are commercially available or are described in the literature or else can be prepared according to methods which are described therein or which are known to a person skilled in the art.

The compounds of general formula (II) can be obtained from commercial sources or can be prepared using methods described in the literature (Sims, J. J. et al., *Tetrahedron Lett.*, 1971, 951).

Another subject-matter of the invention, according to another of its aspects, is the compounds of formulae (Va) and (Vb). These compounds may be of use as intermediates in the synthesis of the compounds of formula (I).

The chemical structures and the physical properties of a few compounds of general formulae (Va) and (Vb) of the invention are illustrated in the following Table 1. The melting points of the products are given in the "M.p." column.

TABLE 1

(Vb) or (Va)

| No.   | $X_1$ | $X_2$ | $X_3$ | $X_4$ | Y                | M.p. (° C.) |
|-------|-------|-------|-------|-------|------------------|-------------|
| Va. 1 | H     | H     | H     | H     | 2-(4-methylphenyl) | 221-222   |
| Vb. 1 | H     | Me    | H     | H     | 3-(pyrid-4-yl)   | 315-316     |
| Va. 2 | H     | F     | H     | H     | 2-(4-fluorophenyl) | 220-221   |
| Vb. 2 | H     | Cl    | H     | H     | 3-(pyrid-4-yl)   | 336-342     |
| Va. 3 | H     | Cl    | H     | H     | 2-(pyrid-4-yl)   | 190-216     |

The preparation of some compounds in accordance with the invention is described in the following examples. These examples are not limiting and only illustrate the present invention. The numbers of the compounds exemplified refer to those given in Tables 1 and 2. The elemental microanalyses, the LC-MS (liquid chromatography coupled to mass spectrometry) analyses and the IR and NMR spectra confirm the structures of the compounds obtained.

EXAMPLE 1

Compound No. 1

7-Fluoro-2-(4-fluorophenyl)-4,5-dihydro-2H-benzo[e]indazol-1-yl N,N-diethylcarbamate 1.1 Methyl 6-fluoro-2-hydroxy-3,4-dihydro-1-naphthoate 12.66 g (316 mmol) of 60% sodium hydride in oil, 900 ml of toluene and 17.69 ml (210 mmol) of dimethyl carbonate are introduced into a 2 l reactor. The reaction mixture is stirred at reflux for 1 h. A solution of 19 g (115 mmol) of 6-fluoro-3,4-dihydro-1H-naphthalen-2-one in 350 ml of toluene is subsequently added. The reaction mixture is heated at reflux for 24 h. The reaction mixture is subsequently cooled to 0° C. and then acidified by addition of 114 ml of acetic acid. 114 ml of water are added and the separated organic phase is separated by settling and washed with two times 150 ml of water and then with 100 ml of a saturated aqueous sodium chloride solution. The organic phase is subsequently dried over magnesium sulphate and then concentrated under reduced pressure to result in 26.1 g of a product which is used as is in the following stage.

1.2 7-Fluoro-2-(4-fluorophenyl)-1-hydroxy-4,5-dihydro-2H-benzo[e]indazole (Va.2)

2 g (9 mmol) of the product obtained in Stage 1.1 and 2.73 g (16.8 mmol) of 4-fluorophenylhydrazine hydrochloride are introduced into a 100 ml reactor. The mixture is dissolved in 100 ml of acetic acid and heated at reflux for 4 h. The reaction mixture is subsequently cooled and then concentrated under reduced pressure. The residue is taken up in 150 ml of ethyl acetate and 100 ml of water. The organic phase is separated by settling and washed twice with 100 ml of water and then once with 100 ml of a saturated aqueous sodium chloride solution. The organic phase is subsequently dried over magnesium sulphate and then concentrated under reduced pressure to result in 3.5 g of the expected compound.

Melting point: 220-221° C.

$^1$H NMR ($d_6$-DMSO): δ (ppm): 2.72 (d×d, 2H), 2.95 (d×d, 2H), 7.01 (m, 2H), 7.3 (m, 2H), 7.75 (m, 3H).

1.3 7-Fluoro-2-(4-fluorophenyl)-4,5-dihydro-2H-benzo[e]indazol-1-yl N,N-diethylcarbamate (Compound No. 1)

3.5 g (9 mmol) of the product obtained in Stage 1.2, 3.48 g (25 mmol) of potassium carbonate and 2.66 ml (21 mmol) of N,N-diethylcarbamoyl chloride are introduced into a 500 ml reactor. The reaction mixture is heated at reflux for 24 h and is then concentrated under reduced pressure. The resulting product is taken up in 100 ml of ethyl acetate. The organic phase is washed twice with 100 ml of water and then once with 100 ml of a saturated aqueous sodium chloride solution. The organic phase is subsequently dried over magnesium sulphate and then concentrated under reduced pressure to result in 5.96 g of crude product. The mixture is purified by chromatography on a silica column, elution being carried out with a mixture of cyclohexane and ethyl acetate. 2.2 g of the expected product are thus isolated and recrystallized from isopropanol to produce 1.5 g (3.77 mmol) of the final product.

Melting point: 141-142° C.

$^1$H NMR (CDCl$_3$): δ (ppm): 1.95 (t, 3H), 2.6 (t, 3H), 2.97 (t, 2H), 3.98 (t, 2H), 3.4 (q, 2H), 3.52 (q, 2H), 7.00 (m, 2H), 7.2 (m, 2H), 7.32 (m, 1H), 7.56 (m, 2H).

EXAMPLE 2

Compound No. 2

7-Fluoro-2-(4-fluorophenyl)-2H-benzo[e]indazol-1-yl N,N-diethylcarbamate

A solution of 0.7 g (1.76 mmol) of 7-fluoro-2-(4-fluorophenyl)-4,5-dihydro-2H-benzo[e]indazol-1-yl N,N-diethylcarbamate, obtained in Stage 1.3 of Example 1, and of 1.2 g (5.2 mmol) of 2,3-dichloro-5,6-dicyano-1,4-benzoquinone in 25 ml of toluene is stirred at reflux for 2 h and then cooled. The mixture is poured onto 100 ml of ethyl acetate. This organic phase is washed with two times 100 ml of a saturated aqueous sodium hydrogencarbonate solution, with 100 ml of water and then with 100 ml of a saturated aqueous sodium chloride solution. The organic phase is separated by settling, then dried over magnesium sulphate and concentrated under reduced pressure. After purification by chromatography on a silica column (eluent: mixture of methylene chloride and of ethyl acetate) and recrystallization from isopropanol, 500 mg (1.26 mmol) of the expected product are obtained.

Melting point: 159-160° C.

$^1$H NMR (d$_6$-DMSO): δ (ppm): 1.04 (t, 3H), 1.21 (t, 3H), 3.28 (q, 2H), 3.55 (q, 2H), 7.45 (m, 3H), 7.7 (m, 5H), 7.9 (d×d, 1H).

EXAMPLE 3

Compounds Nos 3 and 4

7-Chloro-2-(pyrid-4-yl)-4,5-dihydro-2H-benzo[e] indazol-1-yl N,N-diethylcarbamate hydrochloride (Compound No. 3) and 7-chloro-3-(pyrid-4-yl)-4,5-dihydro-3H-benzo[e]indazol-1-yl N,N-diethylcarbamate hydrochloride (Compound No. 4)

3.1 Methyl 6-chloro-2-hydroxy-3,4-dihydro-1-naphthoate 10.1 g (252 mmol) of 60% sodium hydride in oil, 621 ml of toluene and 14.18 ml (163 mmol) of dimethyl carbonate are introduced into a 2 l reactor. The reaction mixture is stirred at reflux for 1 h. A solution of 15.2 g (84 mmol) of 6-chloro-3,4-dihydro-1H-naphthalen-2-one in 268 ml of toluene is subsequently added. The reaction mixture is heated at reflux for 24 h. The reaction mixture is subsequently cooled to 0° C. and then acidified by addition of 92 ml of acetic acid. 114 ml of water are added and the separated organic phase is separated by settling and washed with three times 150 ml of water and then with 100 ml of a saturated aqueous sodium chloride solution. The organic phase is subsequently dried over magnesium sulphate and then concentrated under reduced pressure. The residue is purified by chromatography on a silica column (elution being carried out with a mixture of cyclohexane and of dichloromethane) to result in 12.8 g (53.6 mmol) of the expected product used as is in the following stage.

3.2 7-Chloro-1-hydroxy-4,5-dihydro-2H-benzo[e]indazole 28 g (117 mmol) of the product obtained in Stage 3.1 and 28.6 ml (586.6 mmol) of hydrazine monohydrate are introduced into a 2 l reactor. The mixture is dissolved in 782 ml of acetic acid and heated at reflux for 4 h. The reaction mixture is subsequently cooled and then concentrated under reduced pressure. The resulting product is taken up in 300 ml of ethyl acetate and 300 ml of water. The organic phase is separated by settling and washed twice with 200 ml of water and then once with 200 ml of a saturated aqueous sodium chloride solution. The organic phase is subsequently dried over magnesium sulphate and then concentrated under reduced pressure. The residue obtained is triturated from 200 ml of ethyl ether and then filtered off to result in 25 g (113.3 mol) of the expected product.

Melting point: 232-233° C.

3.3 7-Chloro-1-hydroxy-2-(pyrid-4-yl)-4,5-dihydro-2H-benzo[e]indazole and 7-chloro-1-hydroxy-3-(pyrid-4-yl)-4,5-dihydro-3H-benzo[e]indazole 15.2 g (68.8 mmol) of the product obtained in Stage 3.2, 16.95 g (82.66 mmol) of 4-iodopyridine, 4.14 ml (34.44 mmol) of trans-1,2-diaminocyclohexane, 1.31 g (6.89 mmol) of copper iodide and 36.55 g (172.2 mmol) of potassium phosphate are introduced under an inert atmosphere into a 2 l reactor. The reaction mixture is suspended in 690 ml of dioxane, brought to reflux for 24 h and then cooled. The mixture is concentrated under reduced pressure and then taken up in 200 ml of water. This aqueous phase is acidified to pH 5 by successive additions of acetic acid. The suspension is stirred for 30 minutes and then the precipitate obtained is filtered off, washed with water and then dried under reduced pressure to produce 16.6 g (55.7 mmol) of the expected N-arylation product in the form of a mixture of isomers.

LC-MS: 2 peaks at 60.4% and 38% corresponding to [MH]$^+$=298.

3.4 7-Chloro-2-(pyrid-4-yl)-4,5-dihydro-2H-benzo[e]indazol-1-yl N,N-diethylcarbamate hydrochloride (Compound No. 3) and 7-chloro-3-(pyrid-4-yl)-4,5-dihydro-3H-benzo[e]indazol-1-yl N,N-diethylcarbamate hydrochloride (Compound No. 4)

13 g (43.66 mmol) of the mixture of isomers obtained in Stage 3.3, 18.1 g (131 mmol) of finely ground potassium carbonate and 11.07 ml (87.32 mmol) of N,N-diethylcarbamoyl chloride are introduced, under an inert atmosphere, into a 2 l reactor. The reaction mixture is suspended in 1 l of acetonitrile, brought to reflux for 24 h and then cooled. The reaction mixture is concentrated under reduced pressure. The resulting product is taken up in 300 ml of ethyl acetate and 300 ml of water. The organic phase is separated by settling and washed twice with 200 ml of water and once with 200 ml of a saturated aqueous sodium chloride solution. The organic phase is subsequently dried over magnesium sulphate and then concentrated under reduced pressure. The resulting product comprises the two positional isomers (Compounds Nos 3 and 4). The latter are separated by column chromatography (300 g of Merck 15-40 microns silica, eluents: mixture of heptane and of ethyl acetate).

7-Chloro-2-(pyrid-4-yl)-4,5-dihydro-2H-benzo[e] indazol-1-yl N,N-diethylcarbamate hydrochloride (Compound No. 3)

Product No. 3, thus isolated, is converted to the hydrochloride by dissolving in a 0.1N solution of hydrochloric acid in isopropanol. The solution is concentrated to dryness under reduced pressure. After triturating from ethyl ether, filtering and drying under reduced pressure, 2.3 g (5.79 mmol) of the final product are obtained.

Melting point: 250-251° C.

$^1$H NMR (d$_6$-DMSO): δ (ppm): 1.08 (t, 3H), 1.31 (t, 3H), 2.98 (m, 4H), 3.3 (q, 2H), 3.68 (q, 3H), 7.27 (d, 1H), 7.38 (d×d, 1H), 7.46 (d×d, 1H), 7.92 (d, 2H), 8.87 (d, 2H).

7-Chloro-3-(pyrid-4-yl)-4,5-dihydro-3H-benzo[e] indazol-1-yl N,N-diethylcarbamate hydrochloride (Compound No. 4)

Product No. 4, thus isolated, is converted to the hydrochloride by dissolving in a 0.1N solution of hydrochloric acid in isopropanol. The solution is concentrated to dryness under reduced pressure. After triturating from ethyl ether, filtering and drying under reduced pressure, 6.2 g (15.62 mmol) of the final product are obtained.

Melting point: 224-226° C.

¹H NMR (d₆-DMSO): δ (ppm): 1.18 (t, 3H), 1.29 (t, 3H), 3.02 (t, 2H), 3.31 (m, 4H), 3.51 (q, 2H), 7.20 (d, 1H), 7.32 (dxd, 1H), 7.45 (d, 1H), 8.08 (d, 2H), 8.98 (d, 2H).

EXAMPLE 4

Compound No. 5

8-Methoxy-3-(pyrid-4-yl)-4,5-dihydro-3H-benzo[e]
indazol-1-yl N,N-diethylcarbamate hydrochloride 4.1 Methyl
6-methoxy-2-hydroxy-3,4-dihydro-1-naphthoate 3.4 g (85.12 mmol) of 60% sodium hydride in oil, 180 ml of toluene and 4.78 ml (56.75 mmol) of dimethyl carbonate are introduced into a 1 l reactor. The reaction mixture is stirred at reflux for 1 h. A solution of 5 g (28.37 mmol) of 7-methoxy-3,4-dihydro-1H-naphthalen-2-one in 100 ml of toluene is subsequently added. The reaction mixture is heated at reflux for 24 h. The reaction mixture is subsequently cooled to 0° C. and then acidified by addition of 30 ml of acetic acid. 30 ml of water are added and the separated organic phase is separated by settling and washed with two times 50 ml of water and then with 50 ml of a saturated aqueous sodium chloride solution. The organic phase is subsequently dried over magnesium sulphate and then concentrated under reduced pressure. After purification by chromatography on a silica column (eluent: mixture of methylene chloride and of heptane), 3.9 g (16.64 mmol) of the expected product are obtained and are used as in the following stage.

4.2 1-Hydroxy-8-methoxy-4,5-dihydro-2H-benzo[e]
indazole 3.9 g (16.65 mmol) of the product obtained in Stage 4.1 and 4.06 ml (83.24 mmol) of hydrazine monohydrate are introduced into a 0.5 l reactor. The mixture is dissolved in 166 ml of acetic acid and heated at reflux for 4 h. The reaction mixture is subsequently cooled and then concentrated under reduced pressure. The resulting product is taken up in 100 ml of ethyl acetate and 100 ml of water. The organic phase is separated by settling and washed twice with 100 ml of water and then once with 100 ml of a saturated aqueous sodium chloride solution. The organic phase is subsequently dried over magnesium sulphate and then concentrated under reduced pressure. The residue obtained is triturated from 50 ml of ethyl ether and then filtered off to result in 2.4 g (11.1 mmol) of the expected product.

4.3 1-Hydroxy-8-methoxy-3-(pyrid-4-yl)-4,5-dihy-
dro-3H-benzo[e]indazole 1.2 g (5.55 mmol) of the product obtained in Stage 4.2, 1.36 g (6.66 mmol) of 4-iodopyridine, 0.33 ml (2.77 mmol) of trans-1,2-diaminocyclohexane, 0.105 g (0.55 mmol) of copper iodide and 2.94 g (13.87 mmol) of potassium phosphate are introduced, under an inert atmosphere, into a 0.1 l reactor. The reaction mixture is suspended in 55 ml of dioxane, brought to reflux for 24 h and then cooled. The mixture is subsequently taken up in 1 l of a 1/1 mixture of water and of ethyl acetate. The organic phase is separated by settling and then washed with water (50 ml). This aqueous phase is acidified to pH 5 by successive additions of acetic acid. The precipitate obtained is filtered off, washed with water and then dried under reduced pressure to produce 0.2 g (0.68 mmol) of the expected N-arylation product. The organic phase is dried over magnesium sulphate and then concentrated under reduced pressure. The resulting product is purified by chromatography on a silica column (eluents: mixture of dichloromethane and methanol) to produce an additional 0.57 g (1.94 mmol) of the expected N-arylation product.

¹H NMR (d₆-DMSO): δ (ppm): 2.89 (dxd, 2H), 3.09 (dxd, 2H), 3.73 (s, 3H), 6.2 (dxd, 1H), 7.1 (m, 2H), 7.48 (m, 2H), 8.6 (m, 2H).

4.4 8-Methoxy-3-(pyrid-4-yl)-4,5-dihydro-3H-benzo
[e]indazol-1-yl N,N-diethylcarbamate hydrochloride
(Compound No. 5)

0.77 g (2.63 mmol) of the product obtained in Stage 4.3, 1.09 g (7.88 mmol) of finely ground potassium carbonate and 0.67 ml (5.25 mmol) of N,N-diethylcarbamoyl chloride are introduced, under an inert atmosphere, into a 0.1 l reactor. The reaction mixture is suspended in 30 ml of acetonitrile, brought to reflux for 24 h and then cooled. The reaction mixture is concentrated under reduced pressure. The resulting product is taken up in 100 ml of ethyl acetate and 100 ml of water. The organic phase is separated by settling and washed twice with 50 ml of water and then once with 50 ml of a saturated aqueous sodium chloride solution. The organic phase is subsequently dried over magnesium sulphate and then concentrated under reduced pressure. The resulting product is purified by column chromatography (90 g of Merck 15-40 microns silica, eluents: mixture of heptane and of ethyl acetate). The compound thus isolated is recrystallized from isopropanol and then redissolved in a 0.1N solution of hydrochloric acid in isopropanol. The solution is concentrated to dryness under reduced pressure. After triturating from ethyl ether, filtering off and drying under reduced pressure, 234 mg (0.59 mmol) of the expected compound are obtained.

Melting point: 225-227° C.
¹H NMR (d₆-DMSO): δ (ppm): 1.15 (t, 3H), 1.3 (t, 3H), 2.92 (t, 2H), 3.2-3.4 (m, 4H), 3.51 (q, 2H), 3.71 (s, 3H), 6.8 (m, 2H), 7.2 (d, 1H), 7.98 (d, 2H), 8.82 (d, 2H).

EXAMPLE 5

Compound No. 82

7-Chloro-4,5-dihydro-3-(pyrid-4-yl)-3H-benzo[e]
indazol-1-yl N,N-diisopropylcarbamate hydrochlo-
ride 2.3 g (7.72 mmol) of the mixture of isomers obtained in Stage 3.3 of Example 3, in solution in 30 ml of dimethylformamide, are added dropwise, under an inert atmosphere and at 0° C., to a suspension of 0.4 g (10.04 mmol) of sodium hydride in 17 ml of dimethylformamide in a 1 l reactor. After stirring at ambient temperature for 1 hour, 1.39 g (8.5 mmol) of N,N-diisopropylcarbamoyl chloride in 30 ml of dimethylformamide are added dropwise. The reaction mixture is stirred at ambient temperature for 18 h and is then concentrated under reduced pressure. The resulting product is taken up in 300 ml of ethyl acetate and 300 ml of water. The aqueous phase is brought to pH 5 by addition of acetic acid. The organic phase is separated by settling and washed twice with 200 ml of water and then once with 200 ml of a saturated aqueous sodium chloride solution. The organic phase is subsequently dried over magnesium sulphate and then concentrated under reduced pressure. The resulting product is purified by column chromatography (300 g of Merck 15-40 microns silica, eluents: mixture of dichloromethane and of ethyl acetate). The product thus isolated is converted to the hydrochloride by dissolution in a 0.1N solution of hydrochloric acid in isopropanol. The solution is concentrated to dryness under reduced pressure. After triturating from ethyl ether, filtering off and drying under reduced pressure, 1.2 g (2.6 mmol) of the final product are obtained.

Melting point: 237-269° C.

$^1$H NMR (d$_6$-DMSO): δ (ppm): 1.29 (m, 12H), 3.02 (m, 2H), 3.19 (m, 2H), 3.91 (m, 1H), 4.2 (m, 1H), 7.2 (d, 1H), 7.35 (d×d, 1H), 7.42 (s, 1H), 7.6 (d, 2H), 8.7 (d, 2H).

EXAMPLE 6

Compound No. 84

7-Chloro-3-(pyrid-4-yl)-3H-benzo[e]indazol-1-yl N,N-diisopropylcarbamate hydrochloride 1.65 g (3.38 mmol) of 7-chloro-4,5-dihydro-3-(pyrid-4-yl)-3H-benzo[e]indazol-1-yl N,N-diisopropylcarbamate, prepared according to the method described in Example 5, 1.105 g (6.21 mmol) of N-bromosuccinimide and 0.127 g (0.78 mmol) of 2,2'-azobis(2-methylpropionitrile) are added to a 100 ml reactor. The mixture, dissolved in 40 ml of carbon tetrachloride, is stirred at reflux for 24 h and is then concentrated under reduced pressure. The resulting product is taken up in 300 ml of dichloromethane and 2 ml of a concentrated aqueous ammonia solution. The organic phase is separated and washed with 200 ml of water and then with 200 ml of a saturated aqueous sodium chloride solution. The organic phase is subsequently dried over magnesium sulphate and then concentrated under reduced pressure. The resulting product is purified by chromatography on an alumina column (eluents: mixture of dichloromethane and of methanol) and then on a silica column (eluents: mixture of dichloromethane and of ethyl acetate). The product thus isolated is converted to the hydrochloride by dissolution in a 0.1N solution of hydrochloric acid in isopropanol. The solution is concentrated to dryness under reduced pressure. After triturating from ethyl ether, filtering off and drying under reduced pressure, 1.2 g (2.6 mmol) of the final product are obtained.

Melting point: 234-248° C.

$^1$H NMR (d$_6$-DMSO): δ (ppm): 1.42 (m, 12H), 4.02 (m, 1H), 4.41 (m, 1H), 7.6 (d×d, 1H), 7.8 (m, 3H), 7.92 (d, 2H), 8.15 (d, 1H), 8.79 (d, 2H).

The chemical structures and the physical properties of a few compounds of general formula (I) according to the invention are illustrated in the following Table 2.

In the "Salt" column of this table, "HCl" denotes a hydrochloride and "-" denotes a compound in the base state. The base:acid molar ratios are shown opposite. The "M.p." column gives the melting points of the products, the amorphous compounds being characterized by their mass spectrometry (MS) analytical results.

TABLE 2

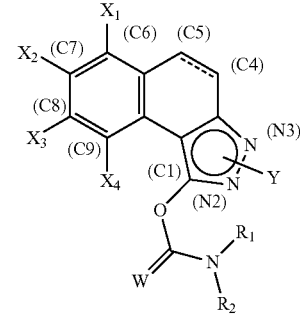

(I)

| No. | X$_1$ | X$_2$ | X$_3$ | X$_4$ | W | NR$_1$R$_2$ | C4-C5 bond | Y | Salt | M.p. (° C.) |
|---|---|---|---|---|---|---|---|---|---|---|
| 1 | H | F | H | H | O | N(CH$_2$CH$_3$)$_2$ | single | 2-(4-fluorophenyl) | — | 141-142 |
| 2 | H | F | H | H | O | N(CH$_2$CH$_3$)$_2$ | double | 2-(4-fluorophenyl) | — | 159-160 |
| 3 | H | Cl | H | H | O | N(CH$_2$CH$_3$)$_2$ | single | 2-(pyrid-4-yl) | HCl 1:1 | 250-251 |
| 4 | H | Cl | H | H | O | N(CH$_2$CH$_3$)$_2$ | single | 3-(pyrid-4-yl) | HCl 1:1 | 224-226 |
| 5 | H | H | OCH$_3$ | H | O | N(CH$_2$CH$_3$)$_2$ | single | 3-(pyrid-4-yl) | HCl 1:1 | 225-227 |
| 6 | H | H | H | H | O | N(CH$_3$)$_2$ | single | 2-(4-methylphenyl) | — | 130-131 |
| 7 | H | H | H | H | O | N(CH$_2$CH$_3$)$_2$ | single | 2-(4-chlorophenyl) | — | 148-149 |
| 8 | H | H | H | H | O | —N(morpholino)O | single | 2-(3-chlorophenyl) | — | 150-151 |
| 9 | H | H | H | H | O | N(CH$_3$)$_2$ | single | 2-(3-chlorophenyl) | — | 128-129 |
| 10 | H | H | H | H | O | N(CH$_2$CH$_3$)$_2$ | single | 2-(3-chlorophenyl) | — | 111-113 |

TABLE 2-continued

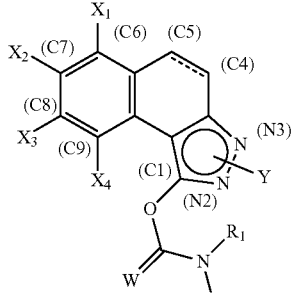

(I)

| No. | X₁ | X₂ | X₃ | X₄ | W | NR₁R₂ | C4-C5 bond | Y | Salt | M.p. (° C.) |
|---|---|---|---|---|---|---|---|---|---|---|
| 11 | H | H | H | H | O | 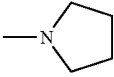 | single | 2-(3-chlorophenyl) | — | 155-157 |
| 12 | H | H | H | H | O | N(CH(CH₃)₂)₂ | single | 2-(3-chlorophenyl) | — | 116-118 |
| 13 | H | H | H | H | O | N(CH₂CH₃)₂ | single | 2-phenyl | — | 124-125 |
| 14 | H | Cl | H | H | O | N(CH₂CH₃)₂ | single | 2-phenyl | — | 114-116 |
| 15 | H | H | H | H | O | N(CH₃)Ph | single | 2-(3-chlorophenyl) | — | 75-78 |
| 16 | H | H | H | H | O | N(CH₂CH₃)₂ | single | 2-(2-chlorophenyl) | — | 396* |
| 17 | H | H | H | H | O | N(CH₂CH₃)₂ | single | 2-ethyl | — | 60-61 |
| 18 | H | H | H | H | O | N(CH₃)Ph | single | 2-ethyl | — | 348* |
| 19 | H | H | H | H | O | N(CH₃)Ph | single | 2-(2,2,2-trifluoroethyl) | — | 402* |
| 20 | H | H | H | H | O | N(CH₂CH₃)₂ | single | 2-(4-fluorophenyl) | — | 132-133 |
| 21 | H | H | H | H | O | N(CH(CH₃)₂)₂ | single | 2-(4-fluorophenyl) | — | 95-96 |
| 22 | H | H | H | H | O | N(CH₃)Ph | single | 2-(4-fluorophenyl) | — | 197-198 |
| 23 | H | H | H | H | O | 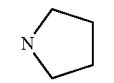 | single | 2-(4-fluorophenyl) | — | 211-212 |
| 24 | H | H | H | H | O | 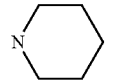 | single | 2-(4-fluorophenyl) | — | 174-175 |
| 25 | H | H | H | H | O |  | single | 2-(4-fluorophenyl) | — | 175-176 |
| 26 | H | H | H | H | O | N(CH₃)₂ | single | 2-(4-chlorophenyl) | — | 211-212 |
| 27 | H | H | H | H | O | N(CH(CH₃)₂)₂ | single | 2-(4-chlorophenyl) | — | 203-204 |
| 28 | H | H | H | H | O | N(CH₃)Ph | single | 2-(4-chlorophenyl) | — | 202-203 |
| 29 | H | H | H | H | O | 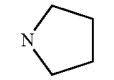 | single | 2-(4-chlorophenyl) | — | 212-213 |
| 30 | H | H | H | H | O | 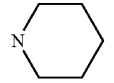 | single | 2-(4-chlorophenyl) | — | 200-201 |

TABLE 2-continued

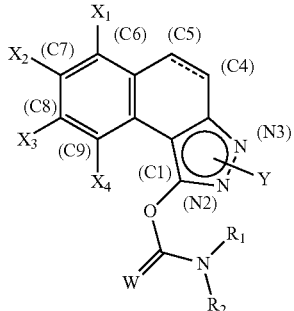

(I)

| No. | X$_1$ | X$_2$ | X$_3$ | X$_4$ | W | NR$_1$R$_2$ | C4-C5 bond | Y | Salt | M.p. (° C.) |
|---|---|---|---|---|---|---|---|---|---|---|
| 31 | H | H | H | H | O |  | single | 2-(4-chlorophenyl) | — | 185-186 |
| 32 | H | H | H | H | O | 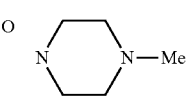 | single | 2-(4-chlorophenyl) | — | 157-158 |
| 33 | H | H | H | H | O | N(CH$_3$)$_2$ | single | 2-(4-fluorophenyl) | — | 216-217 |
| 34 | H | H | H | H | O | 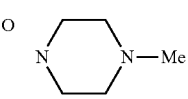 | single | 2-(4-fluorophenyl) | — | 167-168 |
| 35 | H | H | H | H | O | N(CH$_3$)$_2$ | single | 2-phenyl | — | 158-159 |
| 36 | H | H | H | H | O | N(CH(CH$_3$)$_2$)$_2$ | single | 2-phenyl | — | 146-147 |
| 37 | H | H | H | H | O | N(CH$_3$)Ph | single | 2-phenyl | — | 169-170 |
| 38 | H | H | H | H | O |  | single | 2-phenyl | — | 176-177 |
| 39 | H | Cl | H | H | O | N(CH$_2$CH$_3$)$_2$ | single | 2-(4-fluorophenyl) | — | 155-156 |
| 40 | H | H | H | H | O | N(CH$_3$)(CH$_2$)$_2$CH$_3$ | single | 2-(4-fluorophenyl) | — | 143-144 |
| 41 | H | H | H | H | O | N(CH$_2$CH$_3$)$_2$ | single | 2-(3-chloro-4-methylphenyl) | — | 99-101 |
| 42 | H | H | H | H | O | N(CH$_2$CH$_3$)$_2$ | single | 2-(3-chloro-4-fluorophenyl) | — | 148-150 |
| 43 | H | Cl | H | H | O | N(CH$_2$CH$_3$)$_2$ | single | 2-(3-chloro-4-methylphenyl) | — | 131-133 |
| 44 | H | Cl | H | H | O | N(CH$_2$CH$_3$)$_2$ | single | 2-(2,4-difluorophenyl) | — | 78-80 |
| 45 | H | H | H | H | O | N(CH$_2$CH$_3$)$_2$ | single | 2-(pyrid-4-yl) | HCl 1:1 | 298-299 |
| 46 | H | Cl | H | H | O | N(CH$_2$CH$_3$)$_2$ | single | 2-(pyrid-2-yl) | — | 108-110 |
| 47 | H | OCH$_3$ | H | H | O | N(CH$_2$CH$_3$)$_2$ | single | 2-(4-fluorophenyl) | — | 161-162 |
| 48 | H | Br | H | H | O | N(CH$_2$CH$_3$)$_2$ | single | 2-(4-fluorophenyl) | — | 162-163 |
| 49 | H | Cl | H | H | O | N(CH$_2$CH$_3$)$_2$ | single | 2-(3-chloro-4-fluorophenyl) | — | 108-110 |
| 50 | H | Cl | H | H | O | N(CH$_2$CH$_3$)$_2$ | single | 2-methyl | — | 117-118 |
| 51 | H | H | H | H | O | N(CH$_2$CH$_3$)$_2$ | double | 2-(3-chlorophenyl) | — | 125-126 |
| 52 | H | H | H | H | O | N(CH$_2$CH$_3$)$_2$ | double | 2-(4-fluorophenyl) | — | 125-126 |
| 53 | H | H | H | H | O | N(CH$_3$)(CH$_2$)$_2$CH$_3$ | double | 2-(4-fluorophenyl) | — | 154-155 |

TABLE 2-continued

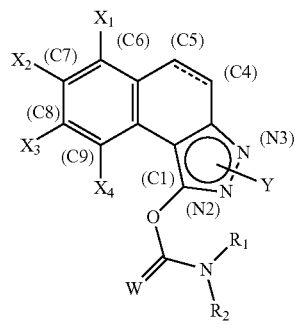

| No. | X₁ | X₂ | X₃ | X₄ | W | NR₁R₂ | C4-C5 bond | Y | Salt | M.p. (° C.) |
|---|---|---|---|---|---|---|---|---|---|---|
| 54 | H | H | H | H | O | N(CH₂CH₃)₂ | double | 2-(3-chloro-4-fluorophenyl) | — | 412* |
| 55 | H | H | H | H | O | N(CH₂CH₃)₂ | double | 2-(3-chloro-4-methylphenyl) | — | 118-120 |
| 56 | H | Cl | H | H | O | N(CH₂CH₃)₂ | double | 2-(4-fluorophenyl) | — | 151-153 |
| 57 | H | Cl | H | H | O | N(CH₂CH₃)₂ | double | 2-(3-chloro-4-fluorophenyl) | — | 141-143 |
| 58 | H | Cl | H | H | O | N(CH₂CH₃)₂ | double | 2-(3-chloro-4-methylphenyl) | — | 141-143 |
| 59 | H | Cl | H | H | O | N(CH₂CH₃)₂ | double | 2-(2,4-difluorophenyl) | — | 144-146 |
| 60 | H | OCH₃ | H | H | O | N(CH₂CH₃)₂ | single | 3-(pyrid-4-yl) | HCl 1:1 | 208-220 |
| 61 | H | CH₃ | H | H | O | N(CH₂CH₃)₂ | single | 3-(pyrid-4-yl) | HCl 1:1 | 222-225 |
| 62 | H | Cl | H | H | O | N(CH₂CH₃)₂ | single | 3-(pyrid-3-yl) | HCl 1:1 | 194-197 |
| 63 | H | Cl | H | H | O | N(CH₂CH₃)₂ | single | 2-(pyrid-3-yl) | HCl 1:1 | 155-157 |
| 64 | H | F | H | H | O | N(CH₂CH₃)₂ | single | 2-(pyrid-4-yl) | HCl 1:1 | 324-326 |
| 65 | H | F | H | H | O | N(CH₂CH₃)₂ | single | 3-(pyrid-4-yl) | HCl 1:1 | 233-242 |
| 66 | H | Cl | H | H | O | N(CH₂CH₃)₂ | single | 3-(4-fluorophenyl) | — | 131-132 |
| 67 | H | Cl | H | H | O | N(CH₂CH₃)₂ | single | 3-(pyrid-2-yl) | HCl 1:1 | 122-123 |
| 68 | H | Cl | H | H | O | N(CH₂CH₃)₂ | single | 2-(3-fluorophenyl) | — | 128-130 |
| 69 | H | Cl | H | H | O | N(CH₂CH₃)₂ | single | 3-(3-fluorophenyl) | — | 124-126 |
| 70 | H | Br | H | H | O | N(CH₂CH₃)₂ | single | 2-(pyrid-4-yl) | HCl 1:1 | 300-310 |
| 71 | H | Br | H | H | O | N(CH₂CH₃)₂ | single | 3-(pyrid-4-yl) | HCl 1:1 | 233-238 |
| 72 | H | Cl | H | H | O | N(CH₂CH₃)₂ | single | 3-(4-methylphenyl) | — | 155-159 |
| 73 | H | Cl | H | H | O | N(CH₂CH₃)₂ | single | 2-(4-methy(phenyl) | — | 118-121 |
| 74 | H | Cl | H | H | O | N(CH₂CH₃)₂ | single | 2-(2-fluorophenyl) | — | 414* |
| 75 | H | Cl | H | H | O | N(CH₂CH₃)₂ | single | 3-(4-chlorophenyl) | — | 177-178 |
| 76 | H | Cl | H | H | O | N(CH₂CH₃)₂ | single | 2-(4-chlorophenyl) | — | 148-149 |
| 77 | H | Cl | H | H | O | N(CH₂CH₃)₂ | single | 2-(4-methoxyphenyl) | — | 131-132 |
| 78 | H | Cl | H | H | O | N(CH₂CH₃)₂ | single | 3-(4-methoxyphenyl) | — | 185-187 |
| 79 | H | Cl | H | H | O | N(CH₂CH₃)₂ | double | 3-(3-fluorophenyl) | — | 142-144 |
| 80 | H | Cl | H | H | O | N(CH₃)Ph | single | 3-(pyrid-4-yl) | — | 213-215 |
| 81 | H | Cl | H | H | O | N(CH(CH₃)₂)₂ | single | 2-(pyrid-4-yl) | — | 184-185 |
| 82 | H | Cl | H | H | O | N(CH(CH₃)₂)₂ | single | 3-(pyrid-4-yl) | — | 146-148 |
|  |  |  |  |  |  |  |  |  | HCl 1:1 | 237-269 |

TABLE 2-continued (I)

| No. | $X_1$ | $X_2$ | $X_3$ | $X_4$ | W | $NR_1R_2$ | C4-C5 bond | Y | Salt | M.p. (° C.) |
|---|---|---|---|---|---|---|---|---|---|---|
| 83 | OCH$_3$ | H | H | H | O | N(CH$_2$CH$_3$)$_2$ | single | 3-(pyrid-4-yl) | HCl 1:1 | 238-240 |
| 84 | H | Cl | H | H | O | N(CH(CH$_3$)$_2$)$_2$ | double | 3-(pyrid-4-yl) | HCl 1:1 | 234-248 |
| 85 | H | Cl | H | H | O | piperidinyl | single | 2-(pyrid-4-yl) | HCl 1:1 | 153-173 |
| 86 | H | Cl | H | H | O | piperidinyl | single | 3-(pyrid-4-yl) | HCl 1:1 | 243-248 |
| 87 | H | Cl | H | H | O | N(CH(CH$_3$)$_2$)$_2$ | single | 2-(pyrid-3-yl) | HCl 1:1 | 243-260 |
| 88 | H | Cl | H | H | O | N(CH(CH$_3$)$_2$)$_2$ | single | 3-(pyrid-3-yl) | HCl 1:1 | 209-213 |
| 89 | H | Cl | H | H | S | N(CH(CH$_3$)$_2$)$_2$ | single | 3-(pyrid-4-yl) | HCl 1:1 | 290-318 |
| 90 | H | Cl | H | H | O | 2,6-dimethylpiperidinyl | single | 3-(pyrid-4-yl) | HCl 1:1 | 228-252 |
| 91 | H | Cl | H | H | O | NCH$_3$C(CH$_3$)$_3$ | single | 2-(pyrid-4-yl) | HCl 1:1 | 350-360 |
| 92 | H | Cl | H | H | O | N(CH(CH$_3$)$_2$)$_2$ | double | 3-(pyrid-3-yl) | HCl 1:1 | 238-240 |
| 93 | H | Cl | H | H | O | N(CH(CH$_3$)$_2$)$_2$ | single | 3-(pyrid-2-yl) | — | 193-195 |
| 94 | H | F | H | H | O | N(CH(CH$_3$)$_2$)$_2$ | single | 3-(pyrid-4-yl) | HCl 1:1 | 255-260 |
| 95 | H | Cl | H | H | O | N(CH(CH$_3$)$_2$)$_2$ | single | 3-(pyrid-2-yl) | — | 220-222 |
| 96 | H | Cl | H | H | O | N(CH(CH$_3$)$_2$)$_2$ | single | 2-(pyrazin-2-yl) | — | 175-176 |
| 97 | H | F | H | H | O | N(CH(CH$_3$)$_2$)$_2$ | double | 3-(pyrid-4-yl) | HCl 1:1 | 272-280 |
| 98 | H | Cl | H | H | O | N(CH(CH$_3$)$_2$)$_2$ | double | 3-(pyrid-2-yl) | — | 213-215 |
| 99 | H | Cl | H | H | O | N(CH$_3$)(C(CH$_3$)$_3$) | single | 3-(pyrid-4-yl) | HCl 1:1 | 411* |
| 100 | H | Cl | H | H | O | N(CH$_2$CH$_3$)$_2$ | double | 3-(pyrid-4-yl) | HCl 1:1 | 227-229 |
| 101 | H | Cl | H | H | O | N(CH$_3$)Ph | double | 3-(pyrid-4-yl) | HCl 1:1 | 248-268 |

*[MH]$^+$

The compounds of the invention have been subjected to pharmacological tests which have demonstrated their advantage as substances with therapeutic activities.

The compounds of the invention also exhibit characteristics of solubility in water which promote good in vivo activity.

Study of the Binding of [$^3$H]Ro5-4864 to Peripheral-Type Benzodiazepine Receptors (PBR or p Sites)

The affinity of the compounds of the invention for PBR or p sites (sites of binding of peripheral type to benzodiazepines) was determined.

The p site receptors can be labelled selectively in rat kidney membranes incubated in the presence of [$^3$H]Ro5-4864. The compounds of the invention have formed the subject of an in vitro study with respect to their affinity for these receptors.

The animals used are male Sprague-Dawley rats (Iffa Credo) weighing 180 to 300 g. After decapitation, the kidney is removed and the tissue is homogenized at 4° C. using a Polytron™ homogenizer for 2 min at 6/10 of the maximum speed in 35 volumes of 50 mM $Na_2HPO_4$ phosphate buffer at a pH adjusted to 7.5 with $NaH_2PO_4$. The membrane homogenate is filtered through gauze and diluted tenfold with buffer.

[$^3$H]Ro5-4864 (specific activity: 70-90 Ci/mmol; New England Nuclear), at a concentration of 0.5 nM, is incubated in the presence of 100 µl of the membrane homogenate in a final volume of 1 ml of buffer comprising the test compound.

After incubating for 3 h at 0° C., the membranes are recovered by filtration through Whatman GF/B™ filters washed with 2 times 4.5 ml of cold (0° C.) incubation buffer. The amount of radioactivity retained by the filter is measured by liquid scintigraphy.

For each concentration of studied compound, the percentage of inhibition of the binding of [$^3$H]Ro5-4864 is determined and then the $IC_{50}$ concentration, the concentration which inhibits 50% of the specific binding, is determined.

The $IC_{50}$ values of the most active compounds of the invention range from 0.5 nM to 300 nM. In particular, compounds Nos 14, 20 and 56 in Table 2 exhibit respective $IC_{50}$ values of 1.6 nM, 2.8 nM and 1.4 nM.

The compounds of the invention are therefore ligands with an affinity for peripheral-type benzodiazepine receptors.

Study of the Neuroprotective Activity

Test of Survival of the Motor Neurons after Sectioning the Facial Nerve in Rats Aged 4 Days After lesion of the facial nerve in immature rats, the motor neurons of the facial nucleus experience neuronal death by apoptosis. Neuronal survival is evaluated using neuronal counting and histological methods.

Immature rats aged 4 days are anaesthetized with pentobarbital (3 mg/kg by the i.p. route). The right facial nerve is exposed and sectioned at its outlet from the stylomastoid foramen. After waking up, the young rats are returned to their mothers and are treated for 7 days with one or two daily administrations, by the oral or intraperitoneal route, at doses ranging from 1 to 10 mg/kg.

7 days after the lesion, the animals are decapitated and the brains are frozen in isopentane at −40° C. The entire facial nerve is cut with a cryostat into sections with a width of 10 µm. The motor neurons are stained with cresyl violet and counted using the Histo™ software (Biocom™)

In this model, the compounds of the invention increase neuronal survival by 38 to 78%. The results of the test of survival of the motor neurons for compounds Nos 14, 20 and 56 of the table are presented in Table 3 below.

TABLE 3

| No. | 14 | 20 | 56 |
|---|---|---|---|
| % increase in the survival of the neurons (10 mg/kg po) | 38% | 59% | 74% |

The results of the tests show that the most active compounds of the invention promote neuroprotection.

The compounds of the invention can thus be used for the preparation of medicaments, in particular for the preparation of a medicament intended to prevent or treat a pathology in which peripheral-type benzodiazepine receptors are involved.

Thus, according to another of its aspects, a subject-matter of the invention is medicaments which comprise a compound of formula (I), or an addition salt of the latter with a pharmaceutically acceptable acid, or a hydrate or a solvate.

These medicaments are employed in therapeutics, in particular in the prevention and/or treatment of various types of peripheral neuropathies, such as traumatic or ischaemic neuropathies, infectious, alcoholic, diabetic, medicinal or genetic neuropathies, and motor neuron conditions, such as spinal amyotrophies and amyotrophic lateral sclerosis. These medicaments will also find an application in the treatment of neurodegenerative diseases of the central nervous system, either of acute type, such as strokes and cranial and medullar traumas, or of chronic type, such as autoimmune diseases (multiple sclerosis), Alzheimer's disease, Parkinson's disease and any other disease in which the administration of neuroprotective/neurotrophic factors is supposed to have a therapeutic effect.

The compounds of the invention can also be used for the preparation of medicaments intended for the prevention and/or treatment of anxiety, of epilepsy and of sleep disorders. This is because ligands of the PBR or p sites stimulate the production of neurosteroids, such as pregnenolone, dehydroepiandrosterone and 3α-hydroxy-5α-pregnan-20-one, by promoting the transfer of cholesterol from the outside to the inside of the mitochondrial membrane. These neurosteroids modulate the activity of the $GABA_A$-chloride channel macromolecular complex and can thus produce anxiolytic, anticonvulsant and sedative activities.

The compounds of the invention can also be used in the treatment of acute or chronic renal insufficiency, of glomerulonephritis, of diabetic nephropathy, of cardiac ischaemia and cardiac insufficiency, of myocardial infarction, of ischaemia of the lower limbs, of coronary vasospasm, of angina pectoris, of pathologies associated with the heart valves, of inflammatory heart diseases, of side effects due to cardiotoxic medicaments or as a result of heart surgery, of atherosclerosis and of its thromboembolic complications, of restenosis, of graft rejections, or of conditions related to incorrect proliferation or incorrect migration of smooth muscle cells.

Furthermore, recent data in the literature indicate that the peripheral-type benzodiazepine receptor might play a fundamental role in the regulation of cell proliferation and cancerization processes. Generally, and in comparison with normal tissues, an increased density of peripheral-type benzodiazepine receptors is observed in various types of tumours and cancers.

In human astrocytomas, the level of expression of the peripheral-type benzodiazepine receptor is correlated with the degree of malignancy of the tumour, the proliferation index and the survival of the patients. In human cerebral tumours, the increase in the number of peripheral-type benzodiazepine receptors is used as a diagnostic indication in medical imaging and as a therapeutic target for conjugates formed from a ligand of the peripheral-type benzodiazepine receptor and from a cytostatic drug. A high density of peripheral-type benzodiazepine receptors is also observed in ovarian carcinomas and breast cancers. As regards the latter, it has been demonstrated that the level of expression of the peripheral-type benzodiazepine receptors is related to the aggressive potential of the tumour; furthermore, the presence of a peripheral-type benzodiazepine receptor agonist stimulates the growth of a mammary cancer line.

These combined results, which suggest a deleterious function of the peripheral-type benzodiazepine receptor in cancerization processes, constitute a relevant basis for the search for synthetic ligands specific for the peripheral-type benzodiazepine receptor which are capable of blocking the effects thereof.

The compounds can therefore be used for the treatment of tumours and cancers.

The peripheral-type benzodiazepine receptors are also present in the skin and, in this respect, the compounds which can be used according to the invention can be used for the prophylaxis or the treatment of cutaneous stress.

The term "cutaneous stress" is understood to mean the various situations which might cause damage, in particular to the epidermis, whatever the agent which causes this stress. This agent can be internal and/or external to the body, such as a chemical or free-radical agent, or else external, such as ultraviolet radiation.

Thus, the compounds which can be used according to the invention are intended to prevent and to combat cutaneous irritation, dry patches, erythemas, dysaesthetic sensations, heating sensations, pruritus of the skin and/or mucous membranes, or ageing, and can also be used in cutaneous disorders, such as, for example, psoriasis, pruriginous diseases, herpes, photodermatoses, atopic dermatitides, contact dermatitides, lichens, prurigo, pruritus, insect stings, in fibroses and other disorders of collagen maturation, in immunological disorders or in dermatological conditions, such as eczema.

The compounds of the invention can also be used for the prevention and treatment of chronic inflammatory diseases, in particular rheumatoid arthritis, and pulmonary inflammatory diseases.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or a solvate of the said compound, and at least one pharmaceutically acceptable excipient. The said excipients are chosen, according to the pharmaceutical form and the method of administration desired, from the usual excipients known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and human beings for the prophylaxis or treatment of the above disorders or diseases.

The appropriate unit administration forms comprise oral forms, such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. The compounds according to the invention can be used, for topical application, in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The said unit forms comprise doses in order to make possible daily administration of 0.001 to 20 mg of active principle per kg of body weight, depending on the pharmaceutical dosage form.

There may be specific cases where higher or lower dosages are appropriate; such dosages do not depart from the scope of the invention. According to the usual practice, the dosage appropriate to each patient is determined by the physician according to the method of administration and the weight and response of the said patient.

The present invention, according to another of its aspects, also relates to a method for the treatment of the pathologies indicated above which comprises the administration, to a patient, of an effective dose of a compound according to the invention, or one of its pharmaceutically acceptable salts or hydrates or solvates.

What is claimed is:
1. A compound of formula (Va):

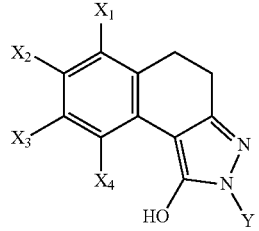

(Va)

in which
$X_1$, $X_2$, $X_3$ and $X_4$ each represent, independently of one another, a hydrogen or halogen atom or a cyano, $C_1$-$C_6$-alkyl, $C_1$-$C_6$-fluoroalkyl, $C_1$-$C_6$-alkoxy or $C_1$-$C_6$-fluoroalkoxy group; and Y represents a $C_1$-$C_6$-alkyl, $C_1$-$C_6$-fluoroalkyl, aryl or heteroaryl group; and wherein the aryl or heteroaryl groups optionally being substituted by one or more atoms or groups selected from halogen atoms, and $C_1$-$C_6$-alkyl, $C_1$-$C_6$-alkoxy, $C_1$-$C_6$-alkylthio, $C_1$-$C_6$-alkyl-S(O)—, $C_1$-$C_6$-alkyl-S(O)$_2$— and $C_1$-$C_6$-fluoroalkyl groups.

2. A compound of formula (Vb)

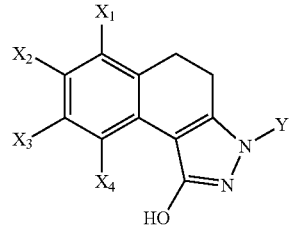

(Vb)

in which
$X_1$, $X_2$, $X_3$ and $X_4$ each represent, independently of one another, a hydrogen or halogen atom or a cyano, $C_1$-$C_6$- alkyl, $C_1$-$C_6$-fluoroalkyl, $C_1$-$C_6$-alkoxy or $C_1$-$C_6$-fluoroalkoxy group; and Y represents an aryl or heteroaryl group; and wherein the aryl or heteroaryl groups optionally being substituted by one or more atoms or groups selected from halogen atoms and $C_1$-$C_6$-alkyl, $C_1$-$C_6$-alkoxy, $C_1$-$C_6$-alkylthio, $C_1$-$C_6$-alkyl-S(O)—, $C_1$-$C_6$-alkyl-S(O)$_2$— and $C_1$-$C_6$-fluoroalkyl groups.

* * * * *

UNITED STATES PATENT AND TRADEMARK OFFICE
CERTIFICATE OF CORRECTION

PATENT NO. : 8,258,168 B2  
APPLICATION NO. : 13/348241  
DATED : September 4, 2012  
INVENTOR(S) : Laurent Dubois et al.

Page 1 of 1

It is certified that error appears in the above-identified patent and that said Letters Patent is hereby corrected as shown below:

Title page, Item (54), and in the Specifications, in column 1, in "Title", line 1, delete "2H" and insert -- 2H- --, therefor.

Title page, Item (75), in column 1, in "Inventors", line 1, delete "Le Piessis-Robinson" and insert -- Le Plessis-Robinson --, therefor.

In the Specifications:

In column 1, line 65, delete "$C_1$-$C_6$alkoxy," and insert -- $C_1$-$C_6$-alkoxy, --, therefor.

In column 2, line 7, delete "$C_t$-$C_z$" and insert -- $C_t$-$C_z$, --, therefor.

In column 17-18, line 23-24, after "methylphenyl" insert -- ) --.

In column 19-20, line 40, delete "2-(4-methy(phenyl)" and insert -- 2-(4-methylphenyl) --, therefor.

Signed and Sealed this  
Seventh Day of May, 2013

Teresa Stanek Rea  
*Acting Director of the United States Patent and Trademark Office*